(12) United States Patent
Detmar et al.

(10) Patent No.: US 11,992,467 B2
(45) Date of Patent: May 28, 2024

(54) PROMOTION OF LYMPHATIC FUNCTION

(71) Applicants: Universitaet Basel, Basel (CH); Eth Zuerich, Zurich (CH)

(72) Inventors: Michael Detmar, Boppelsen (CH); Matthias Hamburger, Oberwil (CH); Olivier Potterat, Aesch (CH); Adriana Sliwa-Primorac, Zurich (CH)

(73) Assignees: Universitaet Basel, Basel (CH); Eth Zuerich, Zurich (CH)

( * ) Notice: Subject to any disclaimer, the term of this patent is extended or adjusted under 35 U.S.C. 154(b) by 76 days.

(21) Appl. No.: 17/652,432

(22) Filed: Feb. 24, 2022

(65) Prior Publication Data

US 2022/0175696 A1    Jun. 9, 2022

Related U.S. Application Data

(63) Continuation of application No. 16/745,949, filed on Jan. 17, 2020, now abandoned, which is a continuation of application No. 14/943,112, filed on Nov. 17, 2015, now abandoned.

(60) Provisional application No. 62/081,218, filed on Nov. 18, 2014.

(51) Int. Cl.
| | | |
|---|---|---|
| *A61K 31/11* | (2006.01) | |
| *A61K 8/34* | (2006.01) | |
| *A61K 36/88* | (2006.01) | |
| *A61Q 19/00* | (2006.01) | |

(52) U.S. Cl.
CPC .............. *A61K 31/11* (2013.01); *A61K 8/34* (2013.01); *A61K 8/345* (2013.01); *A61K 36/88* (2013.01); *A61Q 19/00* (2013.01); *A61K 2236/333* (2013.01); *A61K 2800/10* (2013.01)

(58) Field of Classification Search
None
See application file for complete search history.

(56) References Cited

U.S. PATENT DOCUMENTS

| | | |
|---|---|---|
| 6,224,850 B1 | 5/2001 | Breton et al. |
| 6,471,997 B1 | 10/2002 | Breton et al. |
| 2002/0041908 A1 | 4/2002 | Breton et al. |

FOREIGN PATENT DOCUMENTS

| | | |
|---|---|---|
| EP | 0 797 985 A1 | 10/1997 |
| EP | 0 993 822 A1 | 4/2000 |
| EP | 1 051 965 A2 | 11/2000 |
| EP | 1 174 120 A1 | 1/2002 |
| FR | 2738486 A1 | 3/1997 |
| JP | 62-61924 A | 3/1987 |
| JP | 9-241154 A | 9/1997 |
| KR | 2007-0115507 A | 12/2007 |

OTHER PUBLICATIONS

Benoit-Vical, Françoise, et al., "Antiplasmodial and antifungal activities of iridal, a plant triterpenoid", Phytochemistry, Apr. 2003, pp. 747-751, vol. 62, Elsevier Science Limited, UK.
Bonfils Jean-Paul, et al., "Cytotoxicity of Iridals, Triterpenoids from Iris, on Human Tumor Cell Lines A2780 and K562", Planta Medica, Mar. 2001, pp. 79-81, vol. 67, No. 1., Georg Thieme Verlag, DE.
Halpert, Michal, et al., "Rac-dependent doubling of HeLa cell area and impairment of cell migration and cell cycle by compounds from Iris germanica", Protoplasma, Jan. 2011, pp. 785-797, vol. 248, Springer-Verlag, DE.
Ito, Hideyukiu, et al., "Iridal-Type Triterpenoids with Ichthyotoxic activity from Belamcanda chinensis", Journal of Natural Products, Jan. 1, 1999, pp. 89-93, vol. 62, No. 1, American Chemical Society and American Society of Pharmacognosy, US.
Kraft MD, John, et al., "Review: Management of Acne", CMAJ, Apr. 19, 2011, pp. E430-E435, vol. 183, No. 7, Canadian Medical Association, CA.
Orhan, Ilkay, et al., "Two Isoflavones and Bioactivity Spectrum of the Crude Extracts of Iris Germanica Rhizomes", Phytotherapy Research, Jun. 2003, pp. 575-577, vol. 17, John Whiley & Sons Ltd., UK.
Rahman, A., et al., "Anti-inflammatory isoflavonoids from the rhizomes of Iris germanic," Journal of Ethnopharmacology, vol. 86 (No. 2-3), pp. 177-180, (2003).
Schütz, Cornelia, et al., "Profiling of isoflavonoids in Iris germanica rhizome extracts by microprobe NMR and HPLC-PDA-MS analysis", Fitoterapia, Jun. 2011, pp. 1021-1026, vol. 82, Elsevier B.V., Netherlands.
Turabelidze, Anna, et al., "Inflammation and Wound Healing", Endodontic Topics, Dec. 13, 2012, pp. 26-38, vol. 24, John Whiley & Sons A/S, US.
United States Patent and Trademark Office, Office Action for U.S. Appl. No. 14/943,112, Jan. 9, 2019, 14 pages, U.S.A.
United States Patent and Trademark Office, Office Action for U.S. Appl. No. 14/943,112, filed Sep. 20, 2019, 11 pages, U.S.A.
United States Patent and Trademark Office, Office Action for U.S. Appl. No. 16/745,949, filed Nov. 1, 2021, 5 pages, U.S.A.
Wollenweber, Eckhard, et al., "Cancer chemopreventive in vitro activities of isoflavones isolated from Iris germanica", Planta Medica, Feb. 2003, pp. 15-20, vol. 69, Georg Thieme Verlag Stuttgart, US.
U.S. Appl. No. 16/745,949, filed Jan. 17, 2020, US 2020-0147004 A1, Abandoned.
U.S. Appl. No. 14/943,112, filed Nov. 17, 2015, US 2016-0367499 A1, Abandoned.

*Primary Examiner* — Terry A McKelvey
*Assistant Examiner* — Catheryne Chen
(74) *Attorney, Agent, or Firm* — Alston & Bird LLP

(57) ABSTRACT

The present invention refers to lipophilic extracts of members of the Iridaceae family, such as *Iris germanica* and/or *Iris pallida*, that have been found to promote lymphatic function. These extracts are suitable for the treatment of skin inflammation, rheumatoid arthritis, impaired wound healing, chronic inflammatory diseases, chronic airway inflammation, inflammatory bowel disease, rosacea, primary and/or secondary lymphedemas. The most active components were found to be the iridals.

7 Claims, 10 Drawing Sheets
(3 of 10 Drawing Sheet(s) Filed in Color)

PROMOTION OF LYMPHATIC FUNCTION

CROSS-REFERENCE TO RELATED APPLICATIONS

This application is a continuation of U.S. Non-Provisional application Ser. No. 16/745,949 filed Jan. 17, 2020, which is a continuation of U.S. Non-Provisional application Ser. No. 14/943,112 filed Nov. 17, 2015, which claims priority to U.S. Provisional Application No. 62/081,218 filed Nov. 18, 2014, each of which is hereby incorporated herein in its entirety by reference.

FIELD OF THE INVENTION

The present invention refers to lipophilic extracts of members of the Iridaceae family that have been found to promote lymphatic function.

BACKGROUND OF THE INVENTION

The lymphatic system is part of the circulatory system, comprising a network of conduits called lymphatic vessels that carry a clear fluid called lymph directionally towards the heart. The lymphatic system was first described in the seventeenth century independently by Olaus Rudbeck and Thomas Bartholin. The lymph system is not a closed system. The circulatory system processes up of twenty liters of blood per day through capillary filtration which removes plasma while leaving the blood cells. Some of the filtered plasma actually gets reabsorbed directly into the blood vessels, while the majority of the filtered plasma is left behind in the interstitial fluid. The primary function of the lymph system is to provide a route for this fluid to get returned to the blood.

Lymph is the fluid that is formed when interstitial fluid enters the initial lymphatic vessels of the lymphatic system. The lymph is then moved along the lymphatic vessel network by either intrinsic contractions of the lymphatic vessels or by extrinsic compression of the lymphatic vessels via external tissue forces (e.g. the contractions of skeletal muscles). The organization of lymph nodes and drainage follows the organization of the body into external and internal regions; therefore, the lymphatic drainage of the head, limbs, and body cavity walls follows an external route, and the lymphatic drainage of the thorax, abdomen, and pelvic cavities follows an internal route. Eventually, the lymph vessels empty into the lymphatic ducts, which drain into one of the two subclavian veins (near the junctions of the subclavian veins with the internal jugular veins).

The lymphatic system is involved in the maintenance of the tissue fluid homeostasis, the uptake of dietary fats and the immune response, but its role in diseases has remained unclear for a long time. The recent discovery of lymphatic-specific markers and the development of genetic mouse models with lymphatic phenotypes have advanced the study of the lymphatic system in pathologic conditions.

Impaired lymphatic function results in primary (hereditary) or secondary (acquired) lymphedema—the latter often induced by cancer surgery. Lymphedema is accompanied by fibrosis and susceptibility to inflammation, impaired wound healing and infections. The lymphatic system is also involved in promoting cancer metastasis and in controlling acute and chronic inflammatory diseases, such as psoriasis, chronic airway inflammation, rheumatoid arthritis and inflammatory bowel disease. Moreover, activation of lymphatic vessels has been reported to be beneficial for the treatment of healing wounds, in particular of diabetic wounds. Recent studies on the role of the lymphatic system in lipid homeostasis and fat metabolism have also linked it to obesity and cardiovascular disease. Thus, the modulation of lymphatic function might represent a new strategy for the treatment of a number of inflammatory and neoplastic diseases.

Up to date, several lymphangiogenic factors have been identified. However, only a few of them have been applied in vivo to modulate the function of the lymphatic system in pathologic conditions.

Impaired function of the lymphatic vascular system represents a major health problem. There is currently no cure for lymphedema, which is still treated with palliative methods such as remedial massage and restrictive bandaging. Experimentally, VEGF-C gene transfer via adenoviruses, adeno-associated viruses or naked plasmids, and the application of recombinant VEGF-C protein were successful in animal models for the treatment of diseases related to the lymphatic system. Moreover, combined delivery of AdVEGF-C and lymph node transplantation showed promising results but these results still need to be translated into the clinic. Recently, 9-cis retinoic acid was shown to promote lymphangiogenesis in experimental mouse lymphedema models.

Recent studies revealed that promoting lymphangiogenesis might reduce the extent of chronic inflammation and might promote wound healing. Thus, there is an urgent need for the identification of molecules that promote lymphangiogenesis and that can be applied either topically or systemically.

BRIEF SUMMARY OF THE INVENTION

Provided herein are lipophilic extracts of a member of the Iridaceae family that have been found to promote lymphatic function. The lipophilic extracts can be extracts from *Iris germanica* and/or *Iris pallida*. The presently disclosed extracts are suitable for the treatment of diseases related to impaired lymphatic function in a subject in need thereof, including but not limited to, skin inflammation, rheumatoid arthritis, impaired wound healing, chronic inflammatory diseases, chronic airway inflammation, inflammatory bowel disease, rosacea, primary and/or secondary lymphedemas.

The most active components of the lipophilic extracts were found to be the iridals. Therefore, also provided herein are methods for treating diseases related to impaired lymphatic function by administering one or more iridal to a subject in need thereof.

Cosmetic or pharmaceutical compositions comprising a lipophilic extract of a member of the Iridaceae family or one or more iridal are also provided herewith. Such compositions find use in the treatment of lacrimal sacs, under-eye puffiness, photo-damaged skin, sunburn, skin aging, rosacea, swollen legs, and cellulite.

BRIEF DESCRIPTION OF THE SEVERAL VIEWS OF THE DRAWING(S)

The present invention is further illustrated by means of the following figures. The patent or application file contains at least one drawing executed in color. Copies of this patent or patent application publication with color drawing(s) will be provided by the Office upon request and payment of the necessary fee.

FIG. 1 shows relative results of the sprouting assays performed on the different subfractions of the *Iris germanica* extract obtained by semi-preparative HPLC. Surprisingly, the isoflavone containing fractions did not induce proliferation, migration or sprouting of LECs at concentrations, but it was found that the iridals, which were contained in the more lipophilic fractions, represented the active substance class.

FIG. 2 shows relative results of the proliferation assays described elsewhere herein. VEGF-A (20 ng/ml) and *Iris germanica* extract (25 µg/ml) were compared to the control of 0.1% DMSO. As can be clearly seen from the relative results, VEGF-A enhances the proliferation of all four cell types, whereas the *Iris germanica* extract selectively enhances that of LEC.

FIG. 3a shows crosses obtained in the migration assays, imaged at 5× magnification (0 h and 17 h time points) (Zeiss Axiovert 200 M microscope, Zeiss AxioCam MRm camera, Carl Zeiss A G, Feldbach, Switzerland). As can be seen in FIG. 3a, treatment with *Iris germanica* extract (25 µg/ml) leads to significantly enhanced cell migration.

Figure 3A:
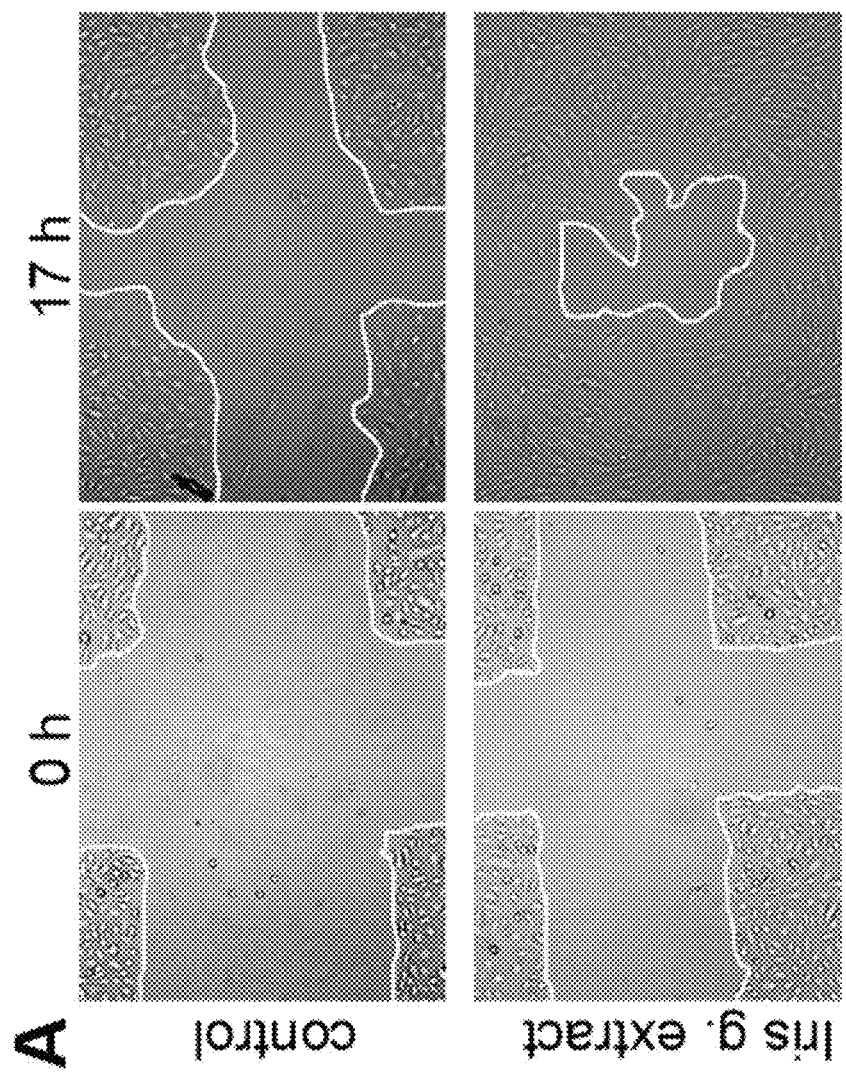
FIGS. 3a and 3b show the results of the migration assay described elsewhere herein.
Figure 3B:
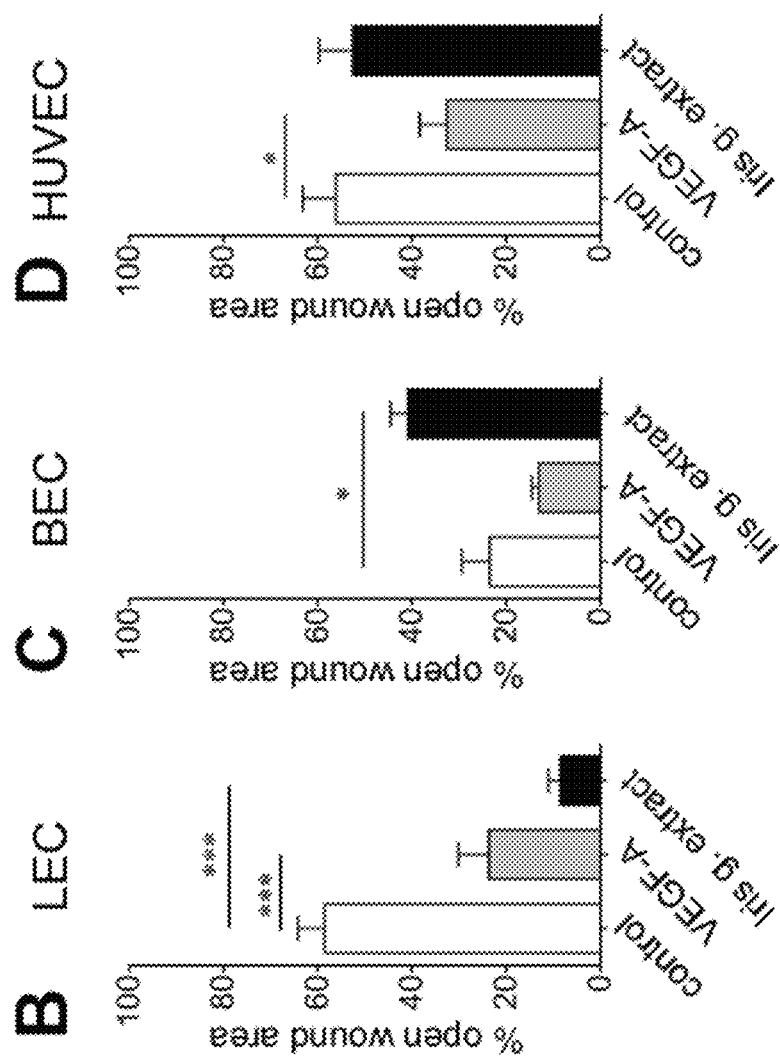

FIG. 3b shows relative results of the migration assays. In FIG. 3b, VEGF-A (20 ng/ml) and *Iris germanica* extract (25 µg/ml) were compared to the control of 0.1% DMSO. Again, VEGF-A enhances the migration of all three cell types, whereas the *Iris germanica* extract selectively enhances that of LEC.

Figure 4:
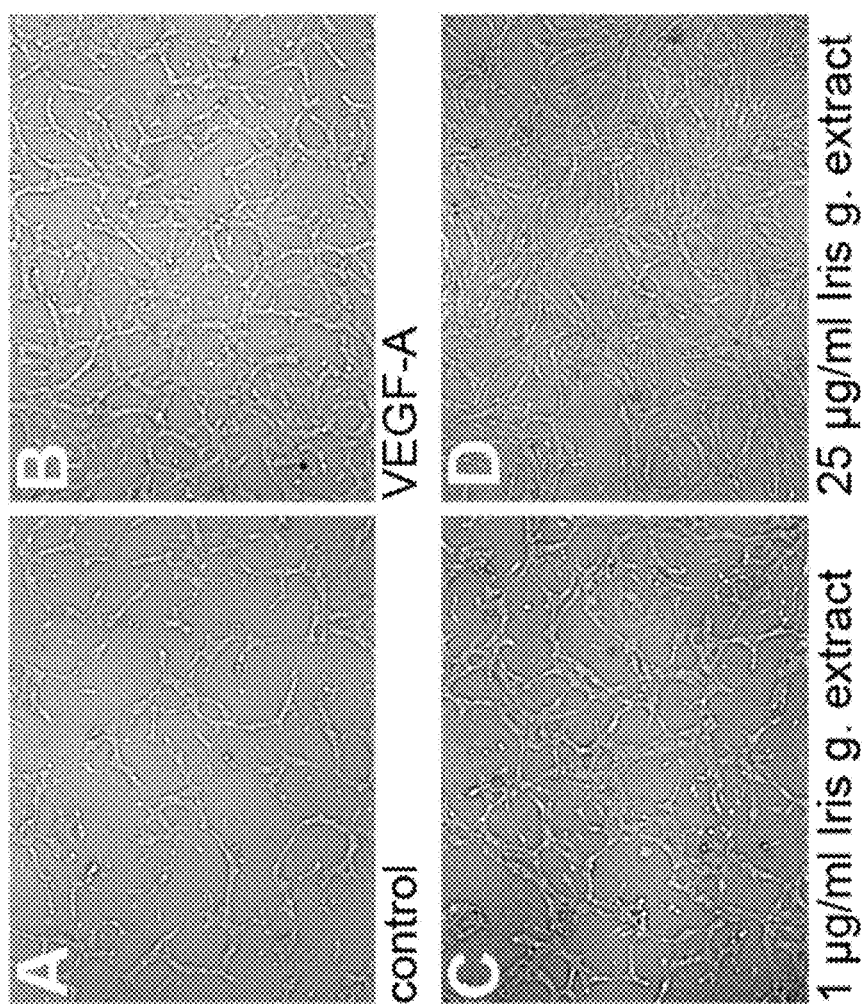

FIG. 4 shows images of the tube formation assays described elsewhere herein, taken at a 5× magnification (Zeiss Axiovert 200 M microscope, Zeiss AxioCam MRm camera). A collagen solution containing type I collagen, 10×PBS, 0.1 M NaOH and 10 M NaOH with or without VEGF-A (20 ng/ml) or *Iris germanica* extract (1 µg/ml and 25 µg/ml, respectively) were compared. Tube formation is clearly enhanced by the solutions containing VEGF-A or *Iris germanica* extract, with the 25 µg/ml *Iris germanica* extract being the most effective.

Figure 5B:
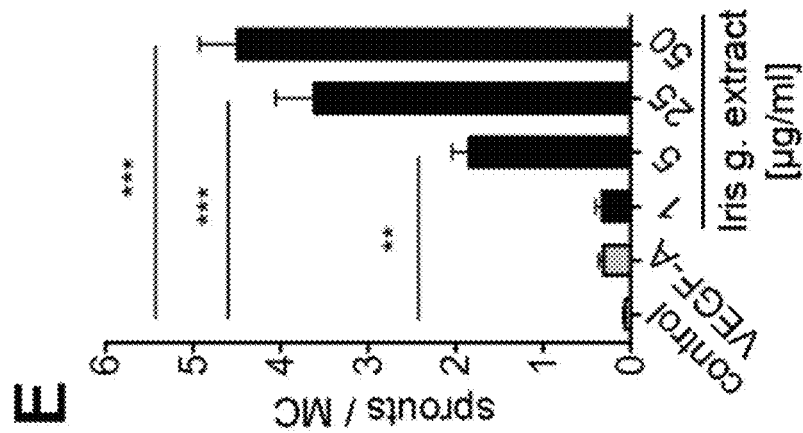
Figure 5A:
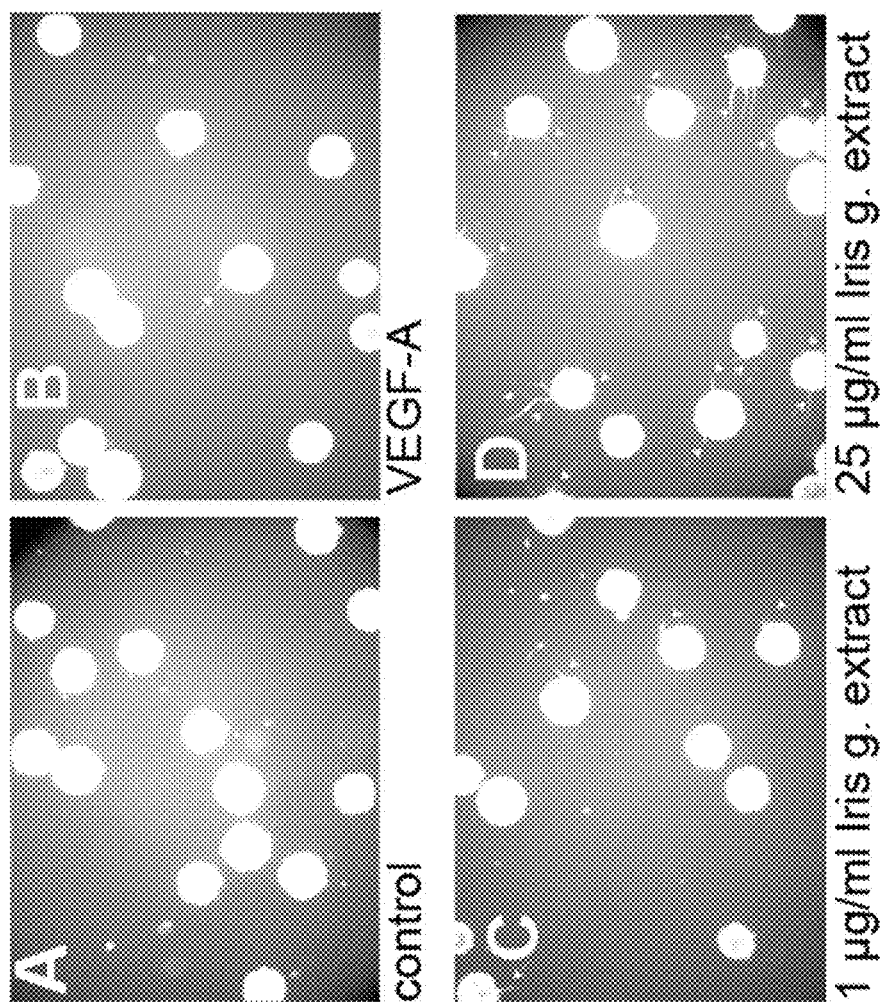

FIGS. 5a and 5b show the results of the sprouting assay described elsewhere herein. FIG. 5a shows images of the induced LEC sprouts of the sprouting assay, imaged at 4× magnification (Molecular Devices ImageXpress Micro HCS microscope MD2, Photometrics CoolSNAP HQ camera, Photometrics, Tucson, AZ, USA). In FIG. 5a, VEGF-A (20 ng/ml) and *Iris germanica* extract (1 µg/ml and 25 µg/ml, respectively) were compared to the control of 0.1% DMSO. Again, treatment with *Iris germanica* extract leads to significantly enhanced sprouting.

FIG. 5b shows relative results of the sprouting assays. The sprouting effect is further quantified in FIG. 5b, where different concentrations of *Iris germanica* extract are found to be more effective than both the control (0.1% DMSO) and VEGF-A.

FIGS. 6a, 6b, 7a, 7b, and 8 show the iripallidal-induced stimulation of lymphangiogenesis and lymphatic function in vivo.

Figure 6A:
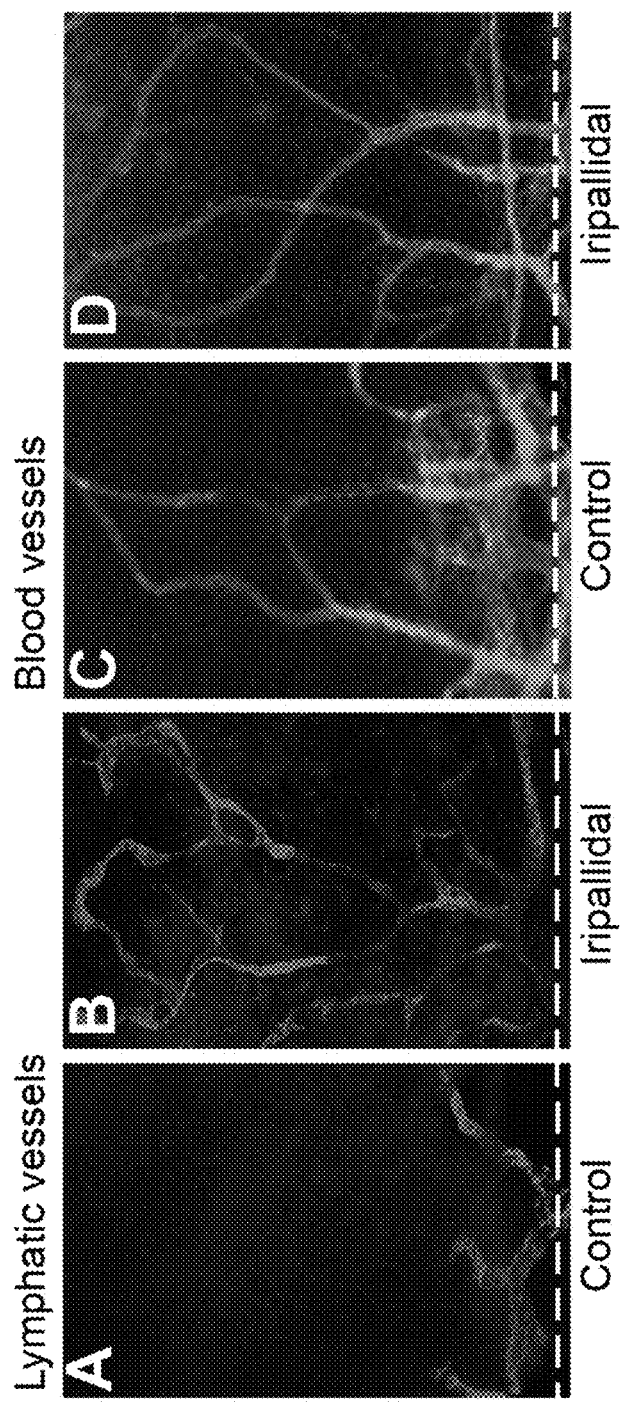
Figure 6B:
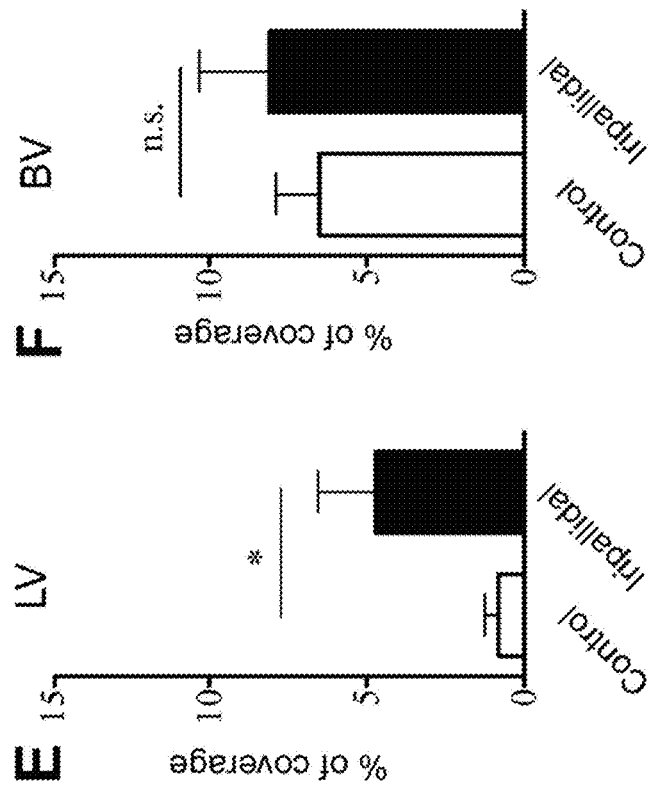

FIG. 6a provides representative immunofluorescence micrographs of the lymphatic vessels (A, B) and blood vessels (C, D) observed in the corneal micropocket assays. These representative immunofluorescence micrographs demonstrate the ingrowth of lymphatic vessels into the cornea at 14 days after implantation of a pellet containing iripallidal (B), but not of a pellet containing DMSO vehicle (A). Similar blood vessel growth occurs into the cornea after implantation of pellets containing DMSO (C) or iripallidal (D). Dotted line: demarcation between cornea and conjunctiva. FIG. 6b shows a summary of repetitive experiments: Lymphatic coverage area (E) was increased after iripallidal treatment (n=9) over control (n=11) (4.7±1.8% vs. 0.8±0.4%, $p<0.05$). No significant difference was observed in blood vessel coverage area (8.1±2.2% vs. 6.5±1.4%, $p=0.53$; F).

FIG. 6b provides quantification of the corneal micropocket assays.

Figure 7A:
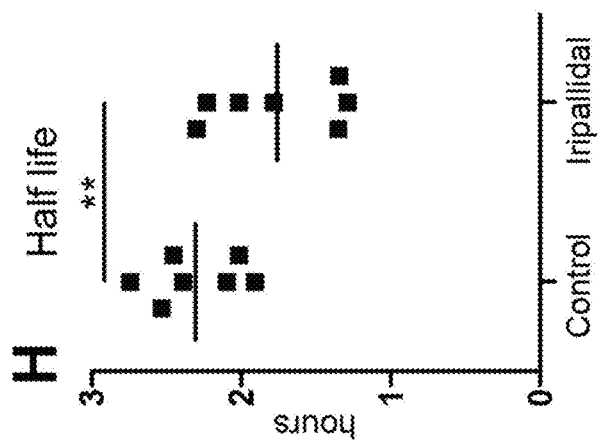
Figure 7B:
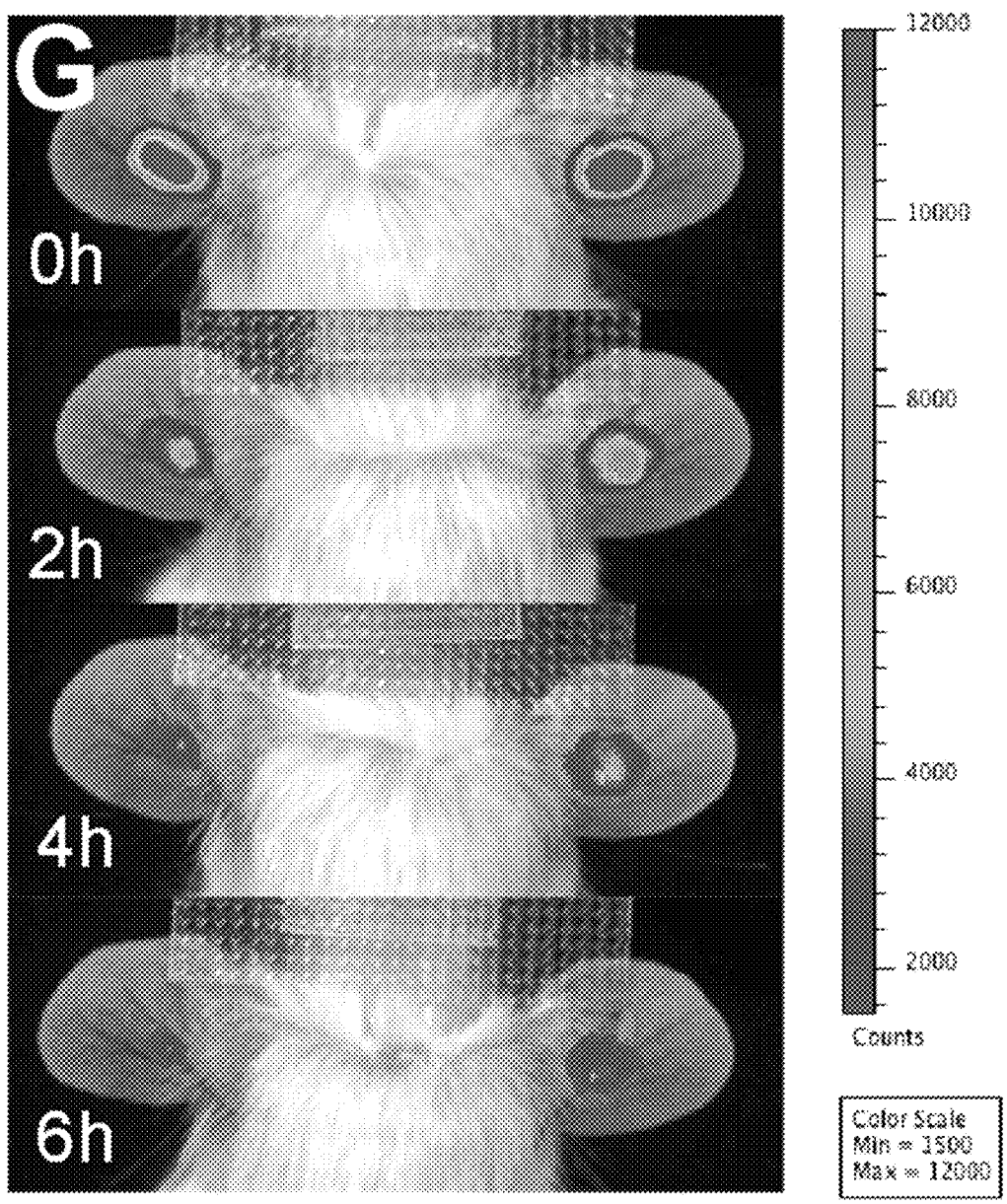

FIGS. 7a and 7b show the results of the lymphatic clearance assays (original magnification ×100). Error bars represent SEM. *$p<0.05$.

FIG. 7a shows the calculated half-life of the lymphatic clearance assays. Fitting the data to a one-phase exponential decay model allowed calculation of half-life of the dye in the tissue, as shown in FIG. 7a.

FIG. 7b shows representative images of dye clearance over time after injection of PEG 20K-IRDye800 into the ear (original magnification ×100). The left ear was treated with iripallidal, the right ear with DMSO control. The decrease of signal intensity compared to baseline was stronger in iripallidal treated ears than in control ears.

Figure 8:
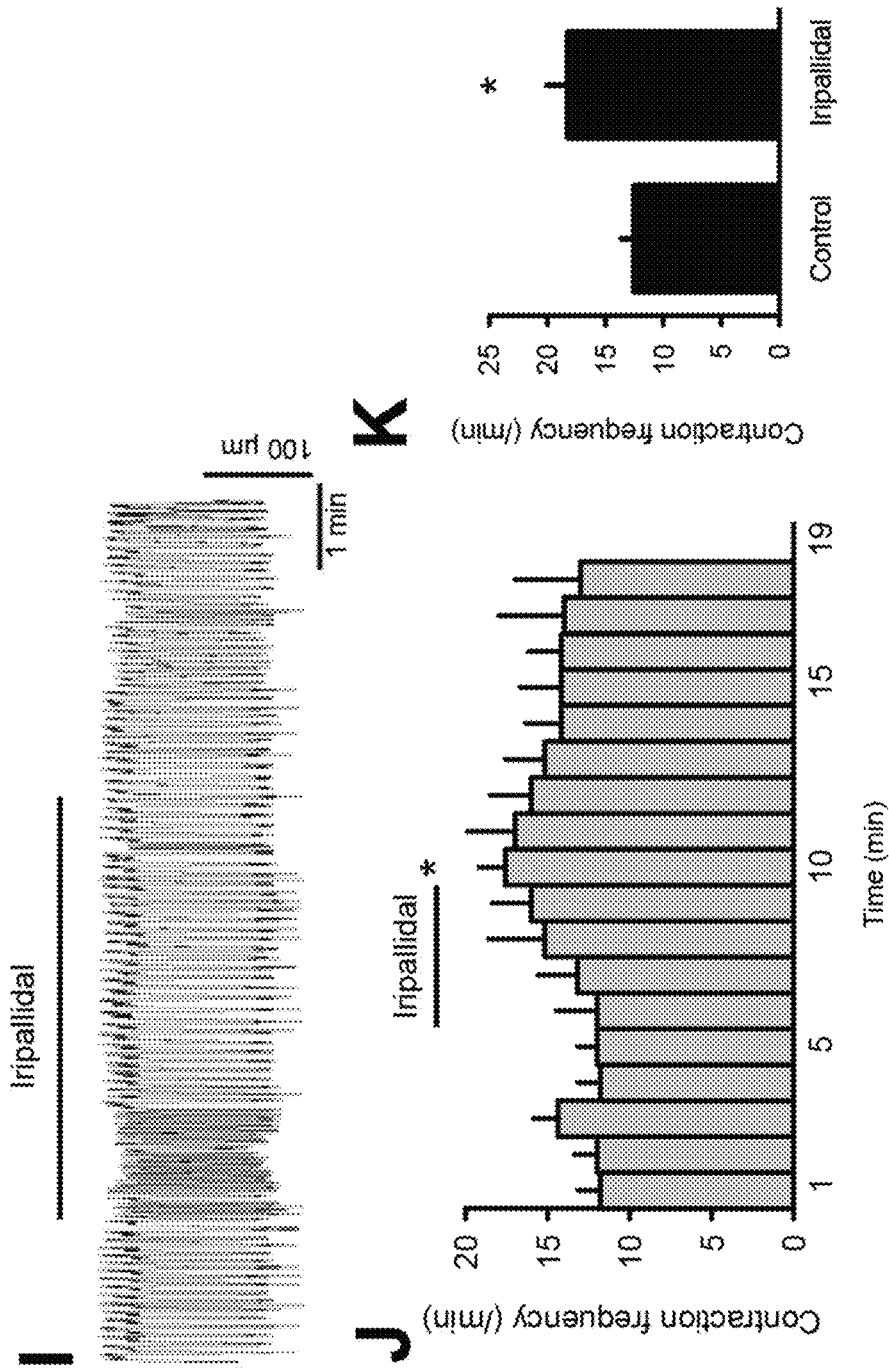

FIG. 8 provides results of the lymphatic contractility assays. The effect of iripallidal on the contractility of guinea pig mesenteric lymphatic vessels is shown in FIG. 8:

Original traces of vessel diameter changes (downward deflections represent contractions) in an actively contracting perfused vessel in response to 10 µM iripallidal, applied for 5 min (horizontal bar) (I).

Time-course histogram of the lymphatic response to iripallidal treatment (10 µm). Columns represent contractions per min (mean±SEM, n=5) (J).

Summary graph of the iripallidal-induced increase in pumping, comparing means (±SEM, n=5) of the 5 min preceding application of iripallidal and the 3 min showing the highest increase in contraction frequency following iripallidal administration. *$p<0.05$.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

It is therefore a problem of the present invention to provide an active agent or composition that can promote lymphatic function and is suitable for cosmetic and/or pharmaceutical applications.

Surprisingly, it has now been found that lipophilic extracts of *Iris germanica* and *Iris pallida* are able to enhance lymphatic function. In particular, they induce proliferation, migration, tube formation and sprouting of human lymphatic endothelial cells (LEC), they induce lymphatic vessel growth, and they promote lymphatic drainage and pumping, processes significantly involved in lymphangiogenesis.

Extracts of members of the Iridaceae family have been described before. In general, they mainly contain isoflavones, acetophenone derivatives, mono- and bicyclic terpenes known as iridals, and about 50% polysaccharides consisting mainly of starch and mucilage.

Most of the previous applications of these extracts focus on the first class of compounds, the isoflavones:

U.S. Pat. No. 6,224,850 discloses the use of an aqueous extract of *Iris pallida* for anti-wrinkle treatment.

U.S. Pat. No. 6,471,997 describes a hydrophilic extract of cells of at least one plant species of the Iridaceae family obtained by in vitro culture, that may be used as an antagonist of CGRP and/or substance P.

US 2002/0041908 refers to Iridaceae extracts for stimulating the immune system.

Six isoflavones isolated from the rhizomes of *Iris germanica* have been examined for their cancer chemopreventive potential (Wollenweber et al. (2003) Cancer chemopreventive in vitro activities of isoflavones isolated from *Iris germanica. Planta Med* 69, 15-20). Three of them—irigenin, irilone, and iriflogenin—were shown to be potent inhibitors of cytochrome P450 1A isoenzyme which is involved in the metabolic conversion of pro-carcinogens to carcinogens.

A chloroform extract and an ethyl acetate extract of the rhizomes of *Iris germanica* were found to possess bactericidal activity (Orhan et al. (2003) Two isoflavones and bioactivity spectrum of the crude extracts of *Iris germanica* rhizomes. *Phytother Res* 17, 575-577). Bioactivity-guided fractionation revealed that this effect was mainly caused by two isoflavones.

Lipophilic and polar extracts of *Iris germanica* rhizomes were submitted to a phytochemical profiling to afford a total of twenty compounds via two successive chromatographic steps (Schutz et al. (2011) Profiling of isoflavonoids in *Iris germanica* rhizome extracts by microprobe NMR and HPLC-PDA-MS analysis. *Fitoterapia* 82, 1021-1026). They were identified as isoflavones, isoflavone glycosides and acetovanillone.

Only very few studies deal with the third class of compounds found in Iridaceae extracts, the iridals:

Ichthyotoxic activity-guided fractionation of the hexane and ether extracts of *Belmacanda chinensis* has resulted in the isolation of elven iridal-type triterpenoids (Ito et al. (1999) Iridal-type triterpenoids with ichthyotoxic activity from *Belmacanda chinensis. J Nat Prod* 62, 89-93).

Iridal, a triterpenoidic compound extracted from *Iris germanica*, has been shown to have an interesting activity on two human tumor cell lines (Bonfils et al. (2001) Cytotoxicity of iridals, plant triterpenoids from *Iris*, on human tumor cell lines A2780 and K562. *Planta Medica* 67, 79-81).

Iridal was also found to have antiplasmodial activity, but no antifungal activity (Benoit-Vical et al. (2003) Antiplasmodial and antifungal activities of iridal, a plant triterpenoid. *Phytochemistry* 62, 747-751).

A lipidic extract from *Iris germanica* was to found to increase HeLa cell area and adhesion and to augment the formation of actin stress fibers (Halpert et al. (2011) Rac-dependent doubling of HeLa cell area and impairment of cell migration and cell cycle by compounds from *Iris germanica. Protoplasma* 248, 785-797). Activity-mediated fractionation and NMR analysis revealed that the active compounds belong to the group of iridals.

In contrast to the above state of the art, the present invention relates to lipophilic extracts of *Iris germanica* and *Iris pallida*, which have been found to promote lymphatic function and are thus suitable for the treatment of diseases related to impaired lymphatic function.

An "extract" in terms of the present invention is the product or mixture obtained by treating an herbal material with a solvent and subsequent recovery of the substances contained in said solvent. Thus, the extract consists of the totality of compounds solubilized in said solvent. Or in other words: The extract is obtainable by extracting an herbal material with a suitable solvent.

In particular, lipophilic extracts of *Iris germanica* and *Iris pallida*—such as those obtained by maceration or accelerated liquid extraction (ASE) of the rhizomes with $CH_2Cl_2$ and those obtained by supercritical fluid extraction (SFE) with $CO_2$—were identified to induce lymphangiogenesis in vitro. Fractionation and functional testing of the different fractions identified iridals, but not isoflavones, as the active molecule class in the extracts. Importantly, one of the identified iridals, iripallidal, potently induced in vivo lymphangiogenesis and also promoted the pumping of isolated lymphatic vessels and the lymphatic fluid drainage from the skin. These findings open new possibilities for promoting lymphangiogenesis in pathologic conditions.

Among the diseases related to impaired lymphatic function that may be treated with the extract of the present invention, especially skin inflammation, rheumatoid arthritis, impaired wound healing, chronic inflammatory diseases, chronic airway inflammation, inflammatory bowel disease, rosacea, primary and/or secondary lymphedemas should be mentioned.

Preferably, the extract of the present invention is a lipophilic extract of the rhizome of *Iris germanica* and/or *Iris pallida*.

In a proliferation assay using human dermal lymphatic endothelial cells (LECs), it has been found that an extract of *Iris germanica* (IG) rhizomes strongly induced the proliferation of lymphatic endothelial cells (LECs) in vitro.

The further investigation of the IG extract in several in vitro lymphangiogenesis assays revealed that it was also able to induce LEC migration, tube formation and sprouting.

Consequently, the extract of the present invention is preferably a lipophilic extract of *Iris germanica*, in particular of the rhizome of *Iris germanica*.

The German iris (*Iris germanica* L., Iridaceae) is a widely distributed ornamental plant. Traditionally, its rhizomes have been used for different topical and oral applications, such as treatment of sores and freckles, as pain relief for teething children, in cosmetic preparations and in perfumery. However, a connection of IG or its extracts with the function of the lymphatic system has not been previously reported.

It was found that iridals, which were contained in the more lipophilic fractions, represented the active substance class.

Therefore, in a further aspect, the present invention also refers to an active agent comprising one or more iridals for the treatment of a disease related to impaired lymphatic function. Preferably, the active agent at least essentially consists of one or more iridals.

These iridals are preferably obtained by plant extraction, in particular from lipophilic extracts of a member of the Iridaceae family. More preferably, the rhizome of said member of the Iridaceae family is extracted.

Alternatively, it would also be possible to prepare them by synthetic or semi-synthetic routes.

An active agent comprising one or more iridals is able to promote lymphatic vessel function and can effectively be used for the treatment of skin inflammation, rheumatoid arthritis, impaired wound healing, chronic inflammatory diseases, chronic airway inflammation, inflammatory bowel disease, rosacea, primary and/or secondary lymphedemas.

In a preferred embodiment, the active agent of the present invention comprises at least one iridal selected from the group consisting of iripallidal, iriflorental, γ-irigermanal, α-irigermanal, the cis isomer of α-irigermanal, the cis isomer of α-dehydroirigermanal, and mixtures thereof. Preferably, the active agent at least essentially consists of one or more iridal(s) selected from the group consisting of iripallidal, iriflorental, γ-irigermanal, α-irigermanal, the cis isomer of α-irigermanal, and the cis isomer of α-dehydroirigermanal.

According to a preferred embodiment, the active agent of the present invention comprises iripallidal. More preferably, the active agent consists at least essentially of iripallidal.

An improvement of lymphatic function has also a positive effect in certain cosmetic applications, such as the treatment of lacrimal sacs—so-called "puffy eyes"—for instance.

Consequently, the extract and active agent of the present invention may also be used for cosmetic treatments.

In a further aspect, the present invention also refers to a cosmetic or pharmaceutical composition comprising the extract of the present invention and/or the active agent of the present invention.

This cosmetic composition of the present invention may be in the form of a watery lotion, an oil-in-water emulsion, a cream or gel containing silicon, a water-in-oil emulsion, a hydroalcoholic lotion or gel, or an anhydrous lotion, gel or stick. Other formulations for topical application may be used.

This cosmetic or pharmaceutical composition may further comprise the additives typically used for the desired application. These are well known to the person skilled in the art.

Pharmaceutical or cosmetic compositions may comprise one or more pharmaceutically or cosmetically acceptable carrier. The term "pharmaceutically acceptable" or "cosmetically acceptable" refers to compositions that are, within the scope of sound medical judgment, suitable for contact with the tissues of human beings and animals without excessive toxicity or other complications commensurate with a reasonable benefit/risk ratio.

"Carriers" as used herein include pharmaceutically or cosmetically acceptable carriers, excipients, or stabilizers that are nontoxic to the cell or mammal being exposed thereto at the dosages and concentrations employed.

Such a carrier includes but is not limited to saline, buffered saline, dextrose, water, glycerol, ethanol, and combinations thereof. The formulation should suit the mode of administration.

In some embodiments, the pharmaceutically or cosmetically acceptable carrier is a non-naturally occurring carrier.

Preferably, the cosmetic composition further comprises one or more additives selected from the group consisting of a sunscreen or sunblock, a skin moisturizer, a skin conditioning agent, a skin exfoliator, an antioxidant, an anti-inflammatory agent, a calming agent, an anti-aging agent, an anti-wrinkling agent, a collagen booster, a peptide, a skin lightening agent, and a skin coloring agent.

These additives include sunscreens or sunblocks for protection against solar radiation, glycerol and humectants to moisturize the skin, niacinamide and other skin conditioning agents, skin exfoliators such as α-hydroxy acids and β-hydroxy acids, antioxidants such as vitamin C and vitamin E, anti-inflammatory and calming agents such as α-bisabolol and caffeine, anti-aging and anti-wrinkling agents such as collagenase inhibitors, collagen boosters and peptides, and skin lightening agents such a kojic acid and mulberry extract. These additives may also be used to impart color or correct color of the skin, such as micronized colored metals, mica and other compounds that absorb or reflect light.

Also, the composition may further comprise additional active ingredients, such as e.g. retinoic acid.

According to a preferred embodiment, the cosmetic or pharmaceutical composition is suitable for topical application. Such a composition can be formulated, e.g., as an oleo creme or hydrocreme, as a massage oil, or in combination with a fatty substance, such as Vaseline, with liposomes, transfersomes or ethosomes.

Alternatively, it would also be possible to formulate the composition for oral or subcutaneous application.

The composition of the present invention may be used for therapeutic and/or cosmetic applications. In particular, it is suitable for the treatment of skin inflammation, rheumatoid arthritis, impaired wound healing, chronic inflammatory diseases, chronic airway inflammation, inflammatory bowel disease, rosacea, primary and/or secondary lymphedemas, as well as for the treatment of lacrimal sacs, under-eye puffiness, photo-damaged skin, sunburn, skin aging, rosacea, swollen legs, and/or cellulite.

Therefore, according to a further aspect of the invention, the above described composition is used for the treatment of lacrimal sacs, under-eye puffiness, photo-damaged skin, sunburn, skin aging, rosacea, swollen legs, and/or cellulite. It has been found that these conditions may be associated with impaired lymphatic vessel function.

In a further aspect, the present invention also refers to a method for the preparation of a lipophilic extract of at least one member of the Iridaceae family, especially for the preparation of the lipophilic extract of the present invention. Preferably, the extract is prepared from the rhizome of said member of the Iridaceae family.

In general, the lipophilic extract of the present invention may be prepared by any of the known extraction techniques that will afford the desired lipophilic fractions, and in particular those containing iridals. Preferably, the rhizome is extracted. Suitable conditions include, e.g. the extraction with $CH_2Cl_2$ and/or ethanol and/or subcritical or supercritical carbon dioxide ($CO_2$).

For obtaining the extracts of the present invention, extraction of the rhizome with $CO_2$ comprising 5 to 10% ethanol has been found to be most effective.

Therefore, in a further aspect, the present invention also refers to a method for the preparation of a lipophilic extract of at least one member of the Iridaceae family, wherein at least a part of the rhizome is extracted with $CO_2$ comprising 5 to 10% ethanol.

In contrast, aqueous or hydro-alcoholic extractions were found to be unsuitable: Extractions with water (100%) or ethanol/water mixtures (25:75, 50:50, and 75:25, respectively)—performed as accelerated solvent extraction (ASE) at 70° C. or as maceration at room temperature—did not afford the desired iridal-containing extracts.

All of the references cited above, as well as all references cited herein, are incorporated herein by reference in their entireties.

All technical and scientific terms used herein have the same meaning. Efforts have been made to ensure accuracy with respect to numbers used (e.g. amounts, temperature, etc.) but some experimental errors and deviations should be accounted for.

It is to be noted that the term "a" or "an" entity refers to one or more of that entity; for example, "a protein" is understood to represent one or more proteins. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

The present invention will be further illustrated by means of the following, non-limiting examples:

EXPERIMENTAL

Materials and Methods
Plant Material

The rhizomes of *Iris germanica* used for extraction were collected in May 2001 in Mamora (Maroc) and identified by Thomas Friedrich (Friedrich Nature Discovery, Euskirchen Germany) or obtained from Dixa AG (Switzerland). Voucher specimens are kept at the Division of Pharmaceutical Biology, University of Basel.

Extraction

Solvent extraction was carried out on an ASE 200 extractor (Dionex) in 18×75 mm cells at 70° C. and a pressure of 120 bar. Three cycles of extraction of 5 min each were performed. Depending on the bath of rhizomes, extraction yields of 6-7% were obtained with $CH_2Cl_2$ and of 26-42% with ethanol. Large scale extraction for iridal identification was performed by percolation or maceration.

Extraction with $CO_2$ and $CO_2$/ethanol was performed in a SFX 220 supercritical fluid extractor (ISCO). The extraction temperature was 50° C. and the restrictor temperature was 150° C. The pressure was set to 690 bar and the flow to 0.6 l/min. The extraction time was 60 min. The extractions yields were 0.3% for $CO_2$, 2.1% for $CO_2$/5% ethanol and 1.6-2.1% for $CO_2$/10% ethanol, respectively.

HPLC-Based Activity Profiling

Iris rhizome powder (30 g) was percolated with 500 ml dichloromethane. A portion (10 mg) of the dichloromethane extract (860 mg) was fractionated by semi-preparative HPLC on a SunFire C18 column (5 μm, 10×150 mm i.d., Waters) equipped with a (10×10 mm) pre-column. A gradient of 20 to 100% aq. acetonitrile in 0.1% aqueous formic acid (5 ml/min) in 30 min was applied. 20 fractions of 90 s each were collected. The fractions were dried and redissolved in DMSO before testing.

Isolation of Iridals

The dried powder rhizomes (884 g) were extracted three times overnight with 4 l, 3.5 l and 3 l of $CH_2Cl_2$, respectively. The combined extracts were evaporated to dryness under reduced pressure to yield 31.6 g of dry extract. The dichloromethane extract was separated in two portions over a Sephadex LH20 column (5×85 cm i.d.) eluted with methanol-$CHCl_3$ 4:1. After TLC analysis ($SiO_2$, chloroform-methanol 97:3, detection with vanillin-sulfuric acid), the fractions containing iridals were combined to provide a crude mixture (5.4 g), which was further separated by preparative HPLC (28 injections) on a SunFire C18 column (5 μm, 30×150 mm, Waters) equipped with a 20×10 mm pre-column. A gradient of 80 to 95% methanol in water over 45 min, followed by 95% methanol for 10 min (20 ml/min) was used for elution. Nine peaks were collected from which ten compounds were finally purified by semi-preparative HPLC (SunFire C18; 5 μm, 10×150 mm i.d. and Atlantis dC18 10×150 mm i.d.) with optimized gradients of acetonitrile or methanol in water: Iridobelamal A (6.6 mg), a mixture of the cis/trans isomers isoiridogermanal and iridobelamal A (32.7 mg), iriflorental (2.7 mg), irisgermanical C (6.4 mg), iripallidal (35.1 mg), irigermanone (6.9 mg), γ-irigermanal (5.3 mg), the cis isomer of α-dehydroirigermanal (5.1 mg) and a mixture of α-irigermanal and its cis isomer (43.6 mg).

Cells

Primary human dermal blood vascular endothelial cells (BEC) and lymphatic endothelial cells (LEC) were isolated from neonatal human foreskins by immunomagnetic purification as described previously (Kajiya et al. (2005) Hepatocyte growth factor promotes lymphatic vessel formation and function. *Embo J* 24, 2885-2895; and Hirakawa et al. (2003) Identification of vascular lineage-specific genes by transcriptional profiling of isolated blood vascular and lymphatic endothelial cells. *The American Journal of Pathology* 162, 575-586).

LECs, BECs and human umbilical vein endothelial cells (HUVECs, Promocell) were cultured in endothelial basal medium (EBM; Lonza, Walkersville, USA) supplemented with 20% fetal bovine serum (FBS), antibiotic antimycotic solution, 2 mM L-glutamine (all from Invitrogen, Pailsey, Scotland), 10 μg/ml hydrocortisone (Sigma-Aldrich, Buchs, Switzerland) and 25 μg/ml N-6,2'-O-dibutyryladenosine 3',5'-cyclic monophosphate (cAMP; Sigma-Aldrich) for up to 11 passages. Cells were grown in plastic dishes coated with type I collagen (50 μg/ml in PBS; Advanced Biomatrix, San Diego, USA).

HaCaT cells, immortalized human epidermal keratinocytes (Boukamp et al. (1988) Normal keratinization in a spontaneously immortalized aneuploid human keratinocyte cell line. *J Cell Biol* 106, 761-771), and primary human dermal fibroblasts, which were manually isolated in our lab, were cultured in Dulbecco's modified Eagle's medium (DMEM, Invitrogen) supplemented with 10% FBS and antibiotic antimycotic solution. Cells were grown in a humidified atmosphere at 37° C. and 5% $CO_2$.

Proliferation, Migration, Tube Formation and Sprouting Assays

Proliferation, migration and tube formation assays were performed as described by Kajiya et al. (2005) Hepatocyte growth factor promotes lymphatic vessel formation and function. *Embo J* 24, 2885-2895.

For all in vitro studies, three independent experiments were performed. Statistical analyses were performed using one-way ANOVA or the two-tailed unpaired Student's t-test (Graph Pad Prism 5).

Proliferation Assay

For proliferation assays, cells ($1.5-3\times10^3$) were seeded onto type I collagen-coated 96-well black, clear-bottom plates (Costar 3603, Corning, NY, USA) and were incubated in endothelial basal medium containing 2% fetal bovine serum and either 0.1% DMSO (Sigma-Aldrich) as vehicle control, VEGF-A (20 ng/ml) as positive control or *Iris germanica* extract (IG extract, 25 μg/ml). After 72 hours, cells were incubated with 4-methylumbelliferylheptanoate (Sigma-Aldrich). The intensity of fluorescence, proportional to the number of viable cells, was measured using a microplate reader (SpectraMax Gemini E M, Molecular Devices, Sunnyvale, USA). Eight replicates per condition were performed.

Figure 2:
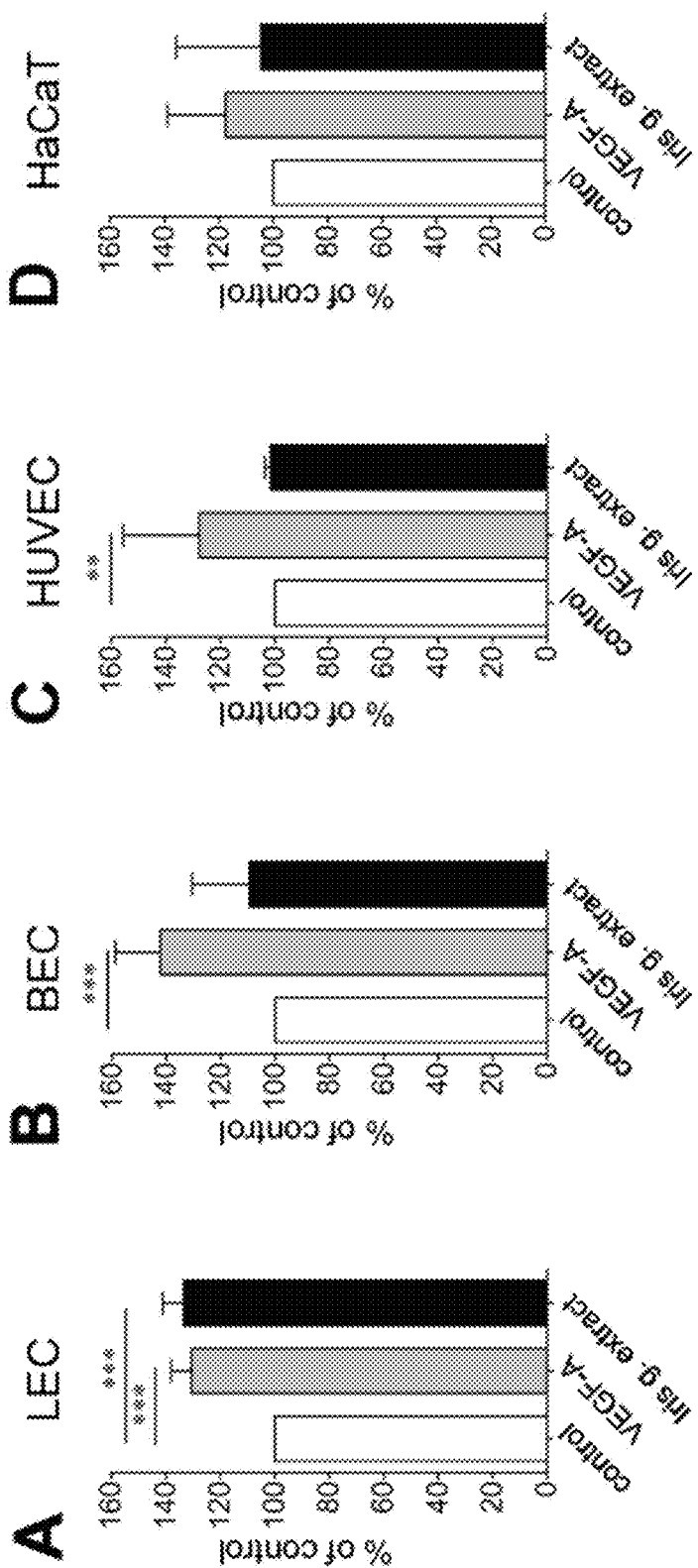

The results of the proliferation assays are shown in FIG. 2.

Migration Assay

The monolayer wound healing ("scratch") assay was performed as described (Geback et al. (2009) TScratch: a novel and simple software tool for automated analysis of monolayer wound healing assays. *Biotechniques* 46, 265-274). Cells (7.5-8×10$^4$) were grown to confluence in 24-well plates and incubated overnight in endothelial basal medium containing 2% fetal bovine serum. Cell monolayers were scratched using a sterile 200 μl pipette tip and washed with PBS. Immediately, the crosses obtained were imaged at 5× magnification (0 h time point) (Zeiss Axiovert 200 M microscope, Zeiss AxioCam MRm camera, Carl Zeiss A G, Feldbach, Switzerland). Following 17 h of incubation with DMSO (0.1%), VEGF-A (20 ng/ml) or the IG extract (25 μg/ml), the same areas were re-imaged (17 h time point). The open wound area was quantified automatically with TScratch. Six replicates per condition were performed.

The results of the migration assays are shown in FIGS. 3*a* and 3*b*.

Tube Formation Assay

The effect of the IG extract on the tube formation of LECs was also assessed. LECs were grown on type I collagen coated 24-well plates until confluence. A collagen solution containing type I collagen, 10×PBS, 0.1 M NaOH and 10 M NaOH with or without VEGF-A (20 ng/ml) or increasing doses of IG extract (1 μg/ml, 5 μg/ml, 25 μg/ml) was overlaid over the cells. After incubation at 37° C. overnight, representative images were taken at a 5× magnification (Zeiss Axiovert 200 M microscope, Zeiss AxioCam MRm camera).

The results of the tube formation assays are shown in FIG. 4.

Sprouting Assay

To investigate cell sprouting, cytodex microcarriers were coated with LECs (Schulz et al. (2012) Phenotype-based high-content chemical library screening identifies statins as inhibitors of in vivo lymphangiogenesis. *Proc Natl Acad Sci USA* 109, E2665-2674). Then, the microcarriers were embedded in a collagen solution and media containing 0.1% DMSO, 20 ng/ml VEGF-A, or different concentrations of the IG extract, its subfractions or iridals were added for 24 hours. The induced sprouts were imaged at 4× magnification (Molecular Devices ImageXpress Micro HCS microscope MD2, Photometrics CoolSNAP HQ camera, Photometrics, Tucson, AZ, USA). Image analysis was performed using ImageJ64 and the number of sprouts per microcarrier was counted and plotted. Three replicates per condition were performed.

The results of the sprouting assays are shown in FIGS. 5*a* and 5*b*.

Corneal Micropocket Assay (TE)

Six to 8-week-old male BALB/c mice (Jackson Laboratory, Bar Harbor, ME) were used for the experiments. All mice were treated according to ARVO Statement for the Use of Animals in Ophthalmic and Vision Research, and all protocols were approved by the Animal Care and Use Committee, University of California, Berkeley. Mice were anesthetized using a mixture of ketamine, xylazine, and acepromazine (50 mg, 10 mg, and 1 mg/kg body weight, respectively) for each surgical procedure. The mouse corneal micropocket assay was performed as described previously (Rogers et al. (2007) The mouse cornea micropocket angiogenesis assay. *Nature protocols* 2, 2545-2550; and Chung et al. (2009) Contribution of macrophages to angiogenesis induced by vascular endothelial growth factor receptor-3-specific ligands. *Am J Pathol* 175, 1984-1992). Briefly, corneal micropockets were created 1.0 mm apart from the limbal vascular arcade using a modified von Graefe Knife. A slow-release pellet of uniformed size was implanted into each pocket. The pellet was made of sucralfate (Sigma Aldrich) and hydron polymer (Sigma Aldrich) containing either 0.8 μg of iripallidal dissolved in DMSO or DMSO alone as a control. Antibiotic ointment (tetracycline) was applied to the eye after pellet implantation and the pellet was left in place for 14 days.

Immunofluorescence Microscopic Assay and Vascular Quantification (TE)

The experiments were performed as described (Ecoiffier et al. (2010) Differential distribution of blood and lymphatic vessels in the murine cornea. *Invest Ophthalmol Vis Sci* 51, 2436-2440; and Grimaldo et al. (2011) Very late antigen-1 mediates corneal lymphangiogenesis. *Invest Ophthalmol Vis Sci* 52, 4808-4812).

Briefly, freshly excised corneas were fixed in acetone for immunofluorescent staining. Nonspecific staining was blocked with anti-Fc CD16/CD32 antibody (BD Biosciences, San Jose, CA). The samples were sequentially stained with FITC-conjugated rat anti-mouse CD31 antibody (Santa Cruz Biotechnology Inc. Santa Cruz, CA) overnight and with purified rabbit anti-mouse LYVE-1 antibody (Abcam, Cambridge, MA), which was visualized by a rhodamine conjugated donkey anti-rabbit secondary antibody. Samples were covered with Vector Shield mounting medium (Vector Laboratories, Burlingame, CA) and examined by an epifluorescence deconvolution microscope (AxioImager M1, Carl Zeiss AG). Vascular structures stained as CD31+ LYVE-1− were identified as blood vessels while those stained as CD31+LYVE-1+ were defined as lymphatic vessels.

Blood and lymphatic vessels were graded and analyzed using the NIH Image J software. The neovascularization area was normalized to the total corneal area to obtain a percentage coverage score for each sample. The neovascularization area refers to the fraction of the corneal area in which vessels are present and the total corneal area was measured by outlining the innermost vessels of the limbal arcade. The statistical significance was evaluated using the student t-test with GraphPad Prism software (GraphPad Software, Inc., La Jolla, CA). $p<0.05$ was considered significant.

The results of these assays are shown in FIGS. 6*a* and 6*b*.

Ex Vivo Lymphatic Contractility Assay

Guinea pigs (7-15 days of age) were killed by decapitation during deep anaesthesia induced by inhalation of isoflurane. The small intestine with its attached mesentery was rapidly dissected and placed in a physiological saline solution (PSS) of the following composition (mM): $CaCl_2$, 2.5; KCl, 5; $MgCl_2$, 2; NaCl, 120; $NaHCO_3$, 25; $NaH_2PO_4$, 1; glucose, 11. The pH was maintained at 7.4 by constant bubbling with 95% $O_2$/5% $CO_2$. Lymphatic tissue was prepared as previously described (von der Weid, P. Y., Crowe, M. J., and Van Helden, D. F. (1996) Endothelium-dependent modulation of pacemaking in lymphatic vessels of the guinea-pig mesentery. *J Physiol* 493 (Pt 2), 563-575); Van Helden, D. F. (1993) Pacemaker potentials in lymphatic smooth muscle of the guinea-pig mesentery. *J Physiol* 471, 465-479; Fox, J. L., and von der Weid, P. Y. (2002) Effects of histamine on the contractile and electrical activity in isolated lymphatic vessels of the guinea-pig mesentery. *Br J Pharmacol* 136, 1210-1218). Briefly, small collecting lymphatic vessels (diameter<230 µm) from the ileal region were dissected together with their associated artery and vein and left intact within the surrounding mesentery, which was used to pin down the tissues on the Sylgard-coated base of a 2-ml organ bath.

The organ bath was then mounted on the stage of an inverted microscope and continuously superfused at a flow rate of 3 ml/min with PSS heated to 36° C. In order to induce a consistent rate of vessel pumping (contraction/relaxation cycle), a fine glass micropipette, connected to an infusion pump via Teflon tubing, was inserted into a cut opening of the vessel in order to perfuse the vessel lumen in the direction of the valves at a flow rate of 2.5 µl/min. This flow rate was very reliable in maintaining a regular rhythmical phasic contractile activity in lymphatic vessels, with contraction frequency usually settling at about 80% of the maximum rate and maintained for the duration of the experiment. Lymphatic vessel chambers were observed by video-microscopy via a camera displaying the image of the vessel on a computer screen. A custom-written MatLab program detected vessel diameter changes on the video image and recorded them as a function of time, allowing measurement of frequency and amplitude of contractions. Decreases in vessel diameter greater than 50% of the diastolic diameter were counted as contractions. Preparations were allowed a 30 min equilibration period prior to drug application during which pumping was assessed. Only vessels reaching a consistent contraction frequency of at least 5 contractions/min during the equilibration period were considered. A 5 min control period of contractile activity was recorded prior to a 1 to 5 min application of iripallidal and effects on vessel contraction frequency were assessed during the ten subsequent minutes.

The results of the contractility assays are shown in FIG. 8.

The animal handling and experiments were approved by the University of Calgary Animal Care and Ethics Committee and conformed to the guidelines established by the Canadian Council on Animal Care.

Lymphatic Clearance Assay

Lymphatic function was assessed by measuring the clearance over time after injection of PEG 20K-IRDye800 into the mouse ear (Proulx et al. (2013) Non-invasive dynamic near-infrared imaging and quantification of vascular leakage in vivo. *Angiogenesis*). Prior to the lymphatic function assessment, ears of seven FVB mice had been treated either with control (DMSO, right ear) or iripallidal (0.9% in DMSO, left ear) once a day for 4 days. Each mouse was anesthetized with isofluorane (2%) and 3 µl of 3 µmol/l PEG 20K-IRDye800 was intradermally injected into the ear with a 30 g syringe. The mouse was then positioned in an IVIS Spectrum (Caliper Life Sciences, Hopkington, MA) and an image was acquired with exposure of 1 s (λex: 745 nm, λem: 800 nm, binning of 4). Subsequent images of the ears were acquired at 1 h, 2 h, 3 h, 4 h, 6 h, and 24 h after injection (FIG. 7b). Mice were allowed to wake up and move freely between imaging time points. Signal intensities were adjusted to baseline ear signals before injection of tracers to calculate tissue enhancement values. The tissue enhancement values at all time points were then normalized to the value directly after injection. Data for each mouse were fit to a one-phase exponential decay model with lymphatic clearance expressed as decay constant K (expressed in h−1) or as half-life (expressed in hours) as shown in equations 1 and 2 (FIG. 7a).

$$\text{Normalized Tissue Enhancement} = e^{-Kt} \quad [1]$$

$$\text{Half Life} = \ln 2/K \quad [2]$$

Results

While the addition of 25 µg/ml *Iris germanica* (IG) extract potently promoted the proliferation of LECs (+33.4±7.7% compared to control, p<0.001), it did not exert significant effects on the proliferation of human blood vascular endothelial cells (BEC), human umbilical vein endothelial cells (HUVEC) and immortalized human epidermal keratinocytes (HaCaT). Thus, the induction seems to be very specific for lymphatic endothelial cells.

LEC migration was studied using the monolayer wound healing ("scratch") assay. Incubation of LECs with 25 µg/ml IG extract potently promoted LEC migration (+50.0%±13.1%, p<0.001).

The effects of the IG extract on LEC tube formation after overlay of LEC monolayers with collagen type I was also investigated: Addition of 1 µg/ml of IG extract overnight potently induced tube formation compared to the DMSO vehicle control. This effect was even stronger after addition of 25 µg/ml of IG extract.

In a 3-dimensional LEC sprouting assay, using LEC-coated microcarriers embedded in a collagen type I gel, it was shown that the IG extract is also able to induce LEC sprouting. After 24 h of incubation, there was a slight induction of LEC sprouting by 1 µg/ml of IG extract. At concentrations of 5, 25 and 50 µg/ml, the IG extract promoted LEC sprouting by 597%±62% (p<0.01), 1168%±143% (p<0.001) and 1453%±140% (p<0.001) compared to VEGF-A induction.

Figure 1:
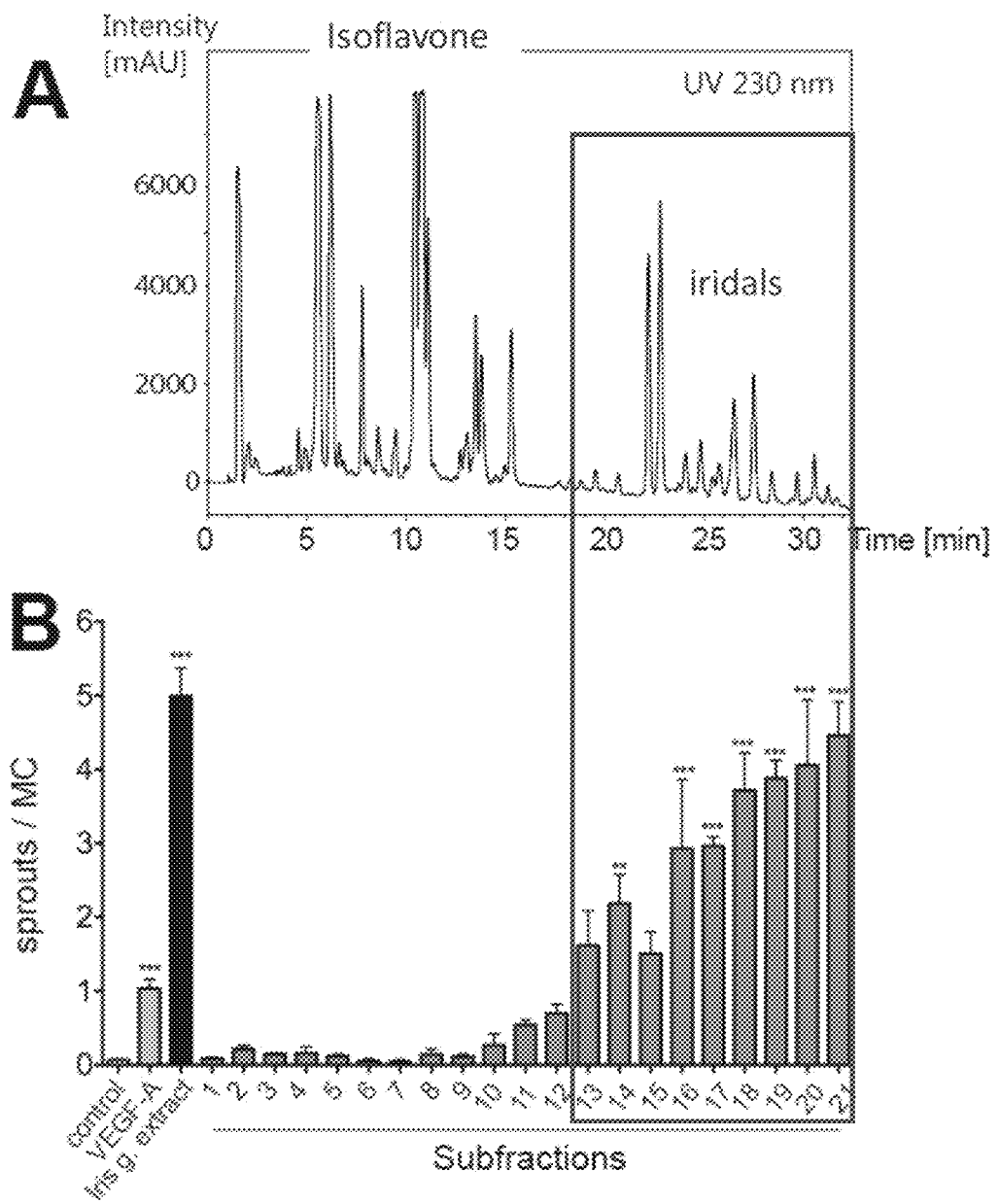

To identify active compounds, the IG extract was profiled by semi-preparative HPLC, followed by functional sprouting assays of the different fractions. The results of these assays are shown in FIG. 1.

It was initially assumed that the main constituents of IG, namely the isoflavones, represent the active compounds, since they have been reported to have anti-inflammatory, immunomodulatory and anti-oxidative properties in vitro. However, isoflavones did not induce proliferation, migration or sprouting of LECs at concentrations from 10 nM to 10 µm, neither as single components nor in combinations.

On the other hand, treatment of LECs with iridal-containing fractions obtained by semi-preparative HPLC could fully reproduce the effects observed with the IG extract. Thus, it was found that iridals, which were contained in the more lipophilic fractions, represented the active substance class.

Nine iridals were then isolated from the IG extract by a combination of chromatographic methods including Sephadex LH-20, and semipreparative and preparative HPLC. All nine compounds significantly promoted LEC sprouting.

In agreement with their slight structural differences, the nine iridals isolated from *Iris germanica* extract showed different minimal effective concentrations:

| Compound | Minimal effective concentration in sprouting assay |
| --- | --- |
| Iridobelamal A | 3 μM |
| Isoiridogermanal and Iridobelamal A (mixture of two cis-trans isomers) | 1 μM |
| Iriflorental | 0.03 μM |
| Irisgermanical C | 1 μM |
| Iripallidal | 0.03 μM |
| Irigermanone | 10 μM |
| γ-irigermanal | 0.01 μM |
| Cis isomer of α-dehydroirigermanal | 0.01 μM |
| α-irigermanal and its cis isomer | 0.01 μM |

As can be seen from the above table, the following six compounds are the most effective sprouting inducers:

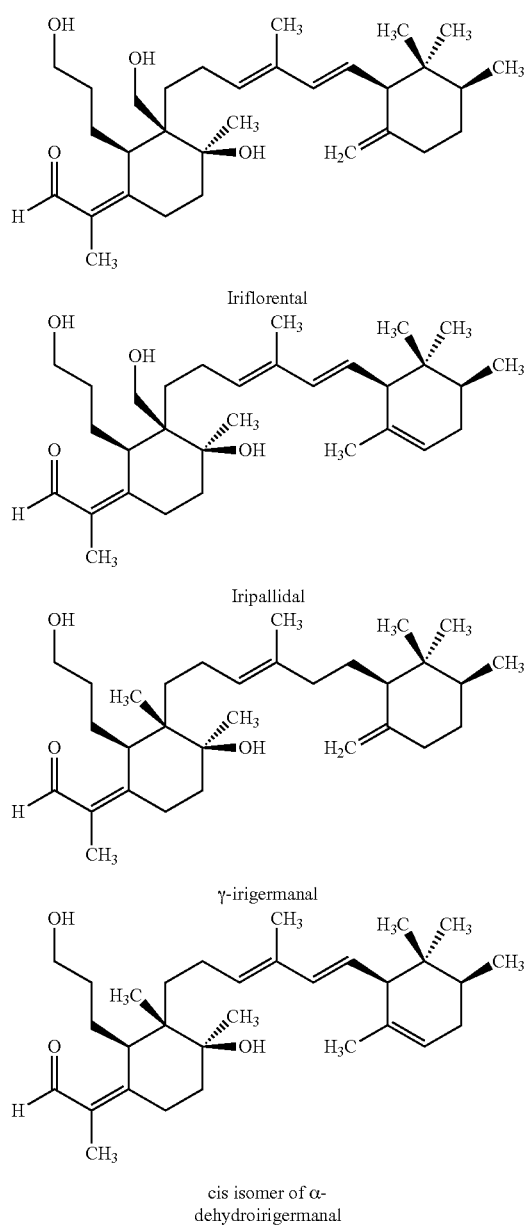

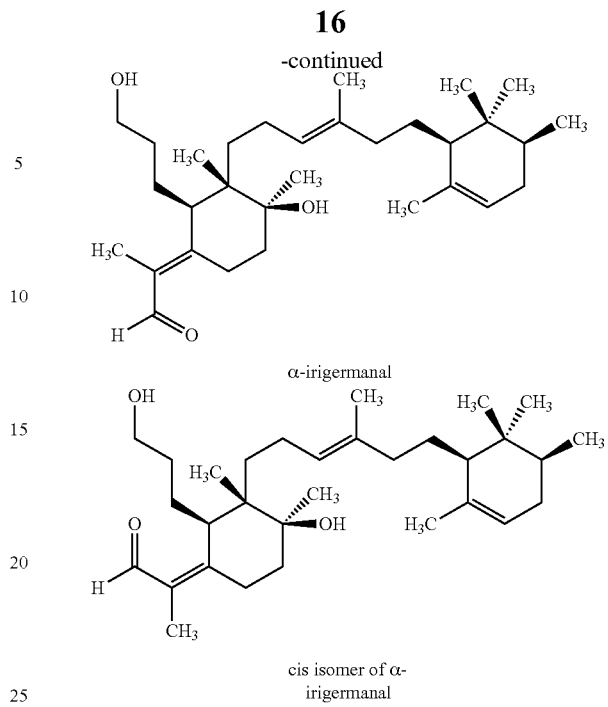

Iripallidal was selected for further in vivo investigations. Using the established mouse cornea lymphangiogenesis assay, it was shown that iripallidal also promotes lymphangiogenesis in vivo: Pellets containing iripallidal or DMSO solvent only were implanted into the corneas of nine mice in the treatment and eleven mice in the DMSO solvent group. After 14 days, the corneas were excised, stained for the lymphatic marker LYVE-1 and the vascular marker CD31, and the corneal area covered by lymphatic or blood vessels was quantified. It was found that pellets containing iripallidal significantly promoted the ingrowth of lymphatic vessels into the cornea (lymphatic vessel coverage of iripallidal treated corneas 4.7%±1.8% vs. DMSO treated 0.8%±0.4%, p=0.0351), whereas no major difference was found regarding the blood vessel coverage area (iripallidal treated corneas 8.1%±2.2% vs. DMSO treated 6.5%±1.4%, p=0.5345). The results of these assays are shown in FIGS. 6a and 6b.

Iripallidal increases the contraction frequency of guinea pig mesenteric lymphatic vessels ex vivo: Guinea pig mesenteric lymphatic vessels displayed a regular rhythmical phasic contractile activity when intraluminally perfused with physiological saline solution (PSS) (von der Weid, P. Y., Crowe, M. J., and Van Helden, D. F. (1996) Endothelium-dependent modulation of pacemaking in lymphatic vessels of the guinea-pig mesentery. *J Physiol* 493 (Pt 2), 563-575); Van Helden, D. F. (1993) Pacemaker potentials in lymphatic smooth muscle of the guinea-pig mesentery. *J Physiol* 471, 465-479; Fox, J. L., and von der Weid, P. Y. (2002) Effects of histamine on the contractile and electrical activity in isolated lymphatic vessels of the guinea-pig mesentery. *Br J Pharmacol* 136, 1210-1218). The contraction frequency reached 13±1 contractions/min (n=10). Administration of iripallidal led in most cases to a small, but significant increase in contraction frequency in 5 out of 6 vessels treated with 10 μM (FIG. 8: I, J, K) and 4 out of 4 vessels treated with 30 μM (data not shown).

Iripallidal also enhances lymphatic drainage function in vivo: The effect of topical iripallidal treatment of the ear skin on the lymphatic drainage function was also investigated:

Control (right ears) or iripallidal (left ears) treatment was applied to the ears of FVB mice for four days once a day (FIG. 7b). At day 4 of treatment, a quantitative lymphatic drainage assay was performed to investigate the removal rate of a lymphatic specific tracer after injection into the ear (FIG. 7a). Ears treated with iripallidal cleared the lymphatic tracer faster than control ears treated with DMSO.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for treating a disease related to impaired lymphatic function comprising administering to a subject in need thereof a lipophilic extract of a member of the Iridaceae family selected from the group consisting of *Iris germanica*, *Iris pallida*, and mixtures thereof, wherein the disease is selected from the group consisting of primary lymphedemas, and secondary lymphedemas.

2. The method of claim 1, wherein said lipophilic extract is a lipophilic extract of the rhizome of the member of the Iridaceae family.

3. The method of claim 1, wherein said lipophilic extract is a lipophilic extract of *Iris germanica*.

4. The method of claim 3, wherein said lipophilic extract is a lipophilic extract of the rhizome of *Iris germanica*.

5. A method for treating a disease related to impaired lymphatic function comprising administering to a subject in need thereof one or more iridals, wherein said disease is selected from the group consisting of primary lymphedemas, and secondary lymphedemas.

6. The method of claim 5, wherein said one or more iridals are selected from the group consisting of iripallidal, iriflorental, $\gamma$-irigermanal, $\alpha$-irigermanal, the cis isomer of $\alpha$-irigermanal, the cis isomer of $\alpha$-dehydroirigermanal, and mixtures thereof.

7. The method of claim 6, wherein said one or more iridals comprises iripallidal.

* * * * *